United States Patent [19]

Bradley

[11] Patent Number: 5,149,634
[45] Date of Patent: Sep. 22, 1992

[54] BIOASSAY FOR ENVIRONMENTAL QUALITY

[75] Inventor: Brian P. Bradley, Ellicott City, Md.

[73] Assignee: The University of Maryland, College Park, Md.

[21] Appl. No.: 339,594

[22] Filed: Apr. 14, 1989

[51] Int. Cl.$^5$ .......................... C12Q 1/02; C12Q 1/00
[52] U.S. Cl. ...................................... 435/29; 435/7.1; 435/7.2; 435/7.21; 435/7.32; 436/86
[58] Field of Search .................... 435/7, 29, 810, 261, 435/7.1, 7.32, 967; 436/811, 815

[56] References Cited

U.S. PATENT DOCUMENTS 4,701,406  10/1987  Chou ..................................... 435/29

FOREIGN PATENT DOCUMENTS 0557098  7/1977  U.S.S.R.

OTHER PUBLICATIONS

Velazquez et al; Cell, vol. 36, pp. 655–662 (1984).
Schlesinger et al; Heat Shock From Bacteria to Man; Cold Spring Harbor Lab; New York (1982) pp. 1, 11, 16, 49.
Hammond et al; Proc. National Academy Sciences, vol. 79, pp. 3485–3488 (1982).
Lambert et al; FEMS (Fed. Eur. Microbiology Society) vol. 56(2), pp. 157–160 (1988).
Webster's New Dictionary of Synomyms, Merriam-Webster, Inc. (1984).
Bournias-Vardiabasis et al, Biological Abstracts, Abstract No. 1926, vol. 83(1), 1987.
Bradley et al, Chemical Abstracts, Abstract No. 21161v, vol. 113, 1989.
Bradley-Marine Environmental Research vol. 28 (1989) pp. 471–475.

Primary Examiner—Sam Rosen
Attorney, Agent, or Firm—Oblon, Spivak, McClelland, Maier & Neustadt

[57] ABSTRACT

A sublethal assay is conducted to determine the presence of a stressor in the environment. An organism exposed to the environment is assayed for the presence of shock proteins, produced in response to environmental stress. The amount of stress protein can be quantified to give an indication of the concentration or amount of stressor, and qualified, by assay for various shock proteins, to give an indication as to the nature of the stressor. The health of an organism may be determined by the assay.

6 Claims, 2 Drawing Sheets

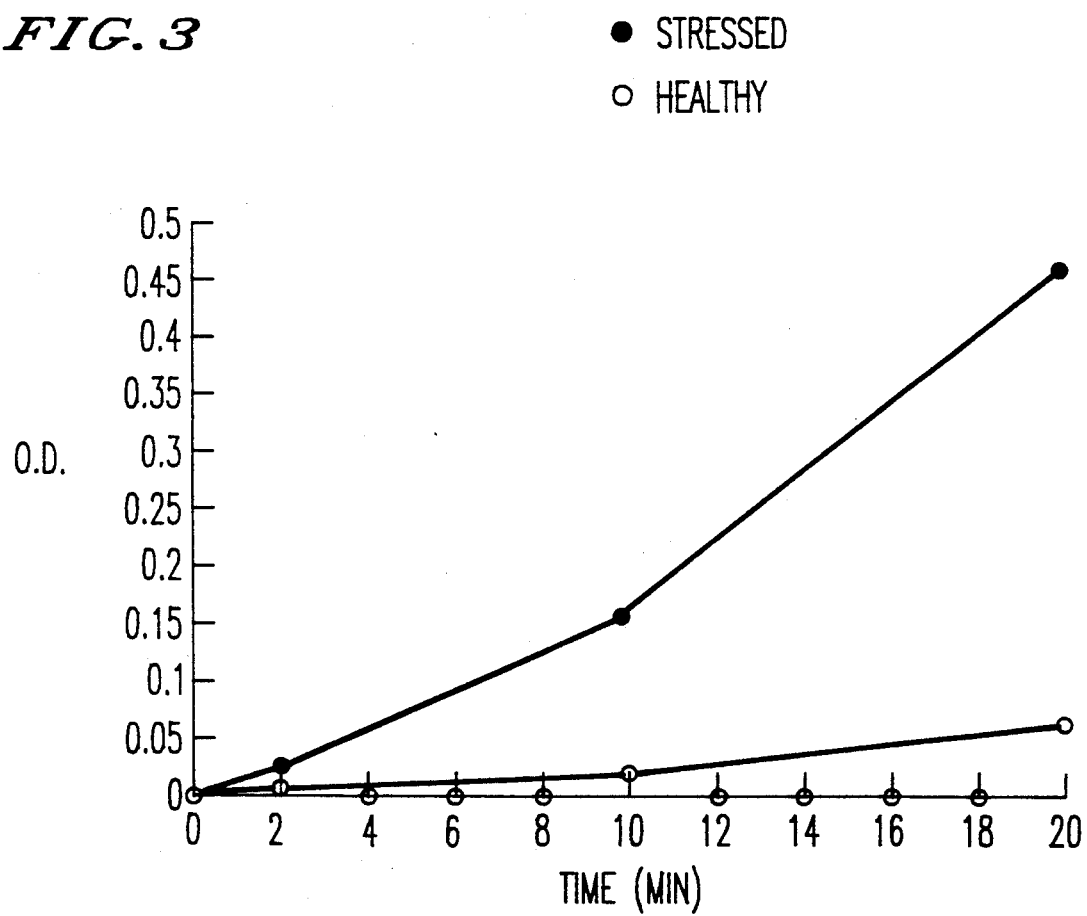

BIOASSAY FOR ENVIRONMENTAL QUALITY

BACKGROUND OF THE INVENTION

1. Field of the Invention

This invention pertains to a sublethal assay to determine environmental quality, and in particular, stress induced through alterations or degradation of the environmental quality. More specifically, organisms in the environment to be studied are assayed for the presence of specific or selected proteins, produced in response to stress. The assay may be used to identify the type of stressor present, or class of stressors.

2. Background of the Prior Art

The continuing and increasing encroachment of industry and civilization on valuable and critical environments inevitably results in a conflict between the ecosystem's ability to maintain a stable environment hospitable to the plants, animals and individuals inhabiting that environment, and the ability of an the industrial complex to distribute or dispose of its waste material, including toxic materials, and environmental pollutants. It is becoming increasingly critical to be able to assay, or periodically sample, the environmental quality, to determine the presence of pollutants, at an early stage, and accordingly take measures to prevent further degradation of the environment. The environment may be aquatic, land, or airborne, or a mixture. It is important to provide an assay system to determine environmental quality that is relatively rapid, low cost, and yet can determine the presence of pollutants at a very early stage and low levels. It would be desirable to provide a system which can provide quantitative measurement of the pollutant and qualitative information as well, such as the type of pollutant actually causing the stress or toxicity.

Some prior art environmental assays are confined to lethal assays. That is, specific laboratory animals are generally exposed to concentrations of the pollutant found in the environment, or actual samples of the environment itself. If the animal or organism survives exposure, it is considered presumptive evidence of no pollution.

One principal drawback to such systems is that acute lethal affects are rarely observed in the field. In general, there is a slow loss of population, corresponding to a gradual increase in or long term exposure to, pollution, until the point at which lethal responses are observed and identified, which is generally beyond the point of no return. In any event, the pollutant or stressor has no gross observable effect (mortality) on the organism at the time of the test. In general, such assays serve only to confirm the investigator's suspicion that there is an environmental pollutant, and that the disappearance of the organism in the environment is not due to some alternative, unexplained natural cause. Other assays require extended exposure (and expense) or sophisticated procedures or equipment not easily accessible.

Accordingly, it remains an objective of the industry to provide an assay based on some criterion other than lethality, or requiring prolonged exposure or impractical end points which can detect the presence of environmental pollutants, or environment changes below lethal levels, give some type of quantitative information regarding the presence of the pollutant, and certain qualitative information, concerning the identity of the pollutant. Environmental managers and aquaculturists may further desire a simple measurement of the health of an organism (commercial animal, human population or other biota).

SUMMARY OF THE INVENTION

A sublethal assay is provided for investigating environmental conditions, and pollution of the environment as well as the health of organisms in the environment. The environment may be aquatic, land, airborne or a mixture wherever the organism is. Specifically, organisms common to the environment are exposed to the ecosystem, or a sample thereof, and subsequently assayed for the presence of selected proteins produced in response to stress. Shock proteins, or stress proteins, appear to be generated in virtually all organisms, in a response to stress. The term stress herein is widely used to include environmental contaminants, such as chemical pollutants and the like, as well as changes in environmental conditions, such as heat, etc. These ubiquitous shock proteins are produced by the organism in response to the environmental change or pollutant (stressor), well in advance of the point at which lethal quantities are encountered in the environment and in advance of outward manifestations of disease and other adverse conditions. The stressor need not be chemical in nature. Any condition which places the organism under stress but does not kill the organism, thereby forcing it to respond to sublethal conditions, may be a stressor. Chemical pollutants, excessive heat or cold, overcrowding, undue and constant noise, perceived threats, all may be considered stressors. Chemical pollutants because of their long term persistence and low visibility, are particularly addressed herein.

The shock proteins appear to be highly conserved across species and genus lines, providing a ready method for sampling diverse environments, allowing diverse organisms (from the environment or the laboratory) as the basis for the assays. Investigation has shown that the production of the shock proteins by the organisms in question is related to the concentration or degree of environmental pollution. Thus, the amount of stress protein produced by the organism gives a direct indication of the degree or severity of the environmental stressor. Additionally, a variety of organisms may be sampled, to determine whether or not the pollutant is toxic, both to the test animal, and other organisms that may be of interest, such as domestic animals, humans and other mammals. Moreover, different pollutants appear to induce the production of different types of shock proteins A variety of shock proteins have been identified, and it appears that there is a family of about 5-10 proteins of relatively large size (40-110 kD, and many smaller shock proteins having a molecular weight below about 25 kD). By determining the specific type of shock protein(s) produced, it is possible to identify the class of pollutant encountered, and accordingly, swiftly identify the source of pollution and take steps to eradicate or correct the environmental pollution experienced.

BRIEF DESCRIPTION OF THE DRAWINGS

FIGS. 1-3 correspond to graphs comparing shock proteins detected in stressed organisms, as opposed to control (unstressed organisms) over time. The method of obtaining the data represented in the drawings is explained in Example I herein.

DETAILED DESCRIPTION OF THE INVENTION

Figure 1:
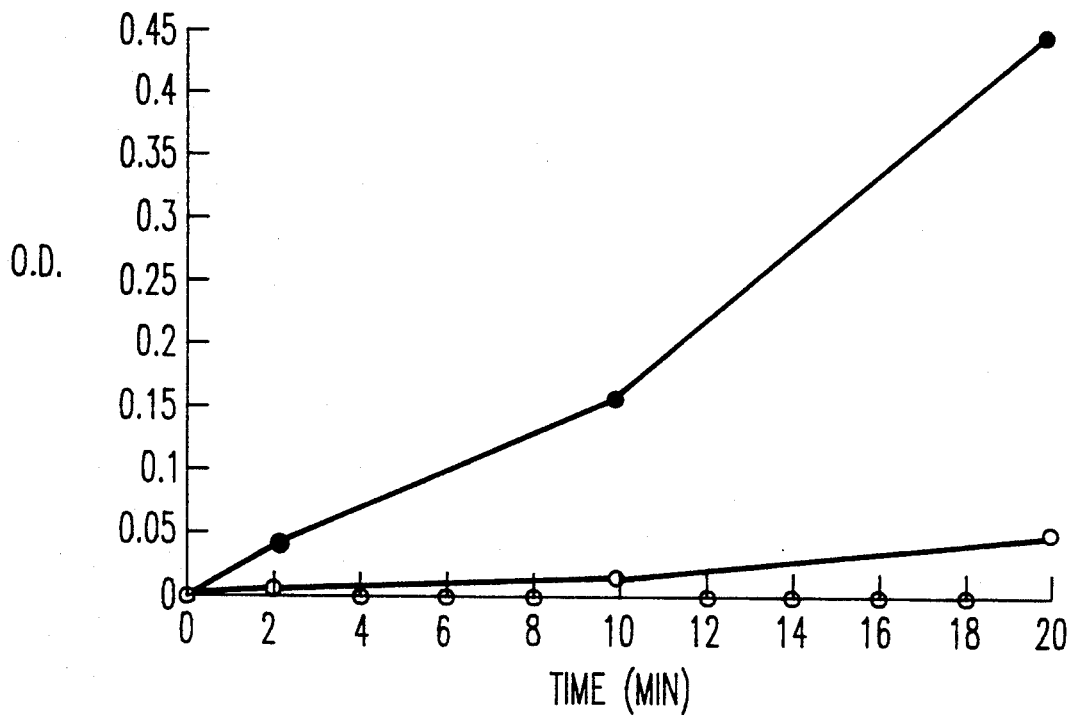

The sublethal assay of the invention relies on the observation that an extraordinarily wide variety of organisms produce, in response to stress induced by the environment, a relatively narrow range of proteins not otherwise produced or expressed, known as shock proteins. Thus, Nover, Heat Shock Response of Eukaryotic Cells, 1984, describes a wide variety of inducers of shock proteins or stressors, and the observed response in a variety of organisms, including vertebrates, ciliates and Drosochila. See in particular, Section 3.1. Again, it is stressed the assay is a sublethal one. Thus, it is not necessary for stress to build to toxic levels or observable symptoms to appear, to use the assay. Indeed, one value of this assay is the early detection of situations which might become lethal in the future.

These shock proteins, in addition to being expressed by virtually all eukaryotes, are highly conserved. Thus, certain shock proteins, such as that identified as Hsp 70 (shock protein having a molecular weight of about 70,000 daltons) is widely observed in a variety of organisms and produced only in response to stress. Thus, specific shock proteins can be assayed for, in organisms exposed to an environment suspected of pollution, and screened for the presence of shock proteins. The presence of shock proteins therein confirms the presence of a pollutant or other stressor, as these proteins are not normally produced by the organisms. The amount of shock protein present correlates directly with the amount of pollutant present, and the family of shock proteins observed gives some indication as to the type of pollutant responsible for the production or the reason for the poor health of an economically important species.

To conduct the assay, the organism may either be cultivated under controlled conditions (laboratory) and then exposed to the environment or taken from the environment directly. In the latter situation, the normal or standard (basal) level for shock protein expression in the organism must be obtained to permit comparison.

A highly sensitive ELISA (enzyme linked immunosorbent assay) can be prepared with an antibody to the shock protein or a peptide characteristic of the shock protein to be assayed for. In the case of Hsp 70, a peptide of 23 amino acids units can be employed to generate an antibody binding thereto. Thus, the antibody will be sensitive to the production of shock proteins in a wide variety of organisms.

It should be noted that these peptides will be generally recognized by the organism that is employed as the host for the production of the antibody, as the high degree of conservation of these peptides results in the immune systems of the host animal being responsive to the peptide in question. Thus, a conjugate of peptide and some other antigen, which may be linked, e.g., covalently, such as bovine serum albumin BSA for non-bovine hosts should be used. This conjugant can be injected into a suitable host such as rabbits or mice and antibodies obtained in the serum thereof, according to conventional procedures. The antibody need not be monoclonal, and polyclonal antibodies can be readily obtained from suitable hosts, without complicated purification systems. Moreover, there is no need to maintain a ready deposit of cells expressing the antibody, they can be obtained as needed.

In practice, the antibody itself is bound to a support such as polystyrene balls, microtiter plates, etc. The bound antibody preparation is then contacted with the tissue sample drawn from the organism used as the base of the assay, previously exposed to the environment in question. Shock protein, if present, will bind to the antibody, a binding which may be subsequently determined by conventional standard sandwich assays, chromatic assays and the like. Virtually any reagent giving a detectible reaction may be used as a marker. It is apparent that this assay can be used to monitor for the presence of persistent or widely used chemicals in the environment, such as pesticides collected in water run-off, etc. As noted, the assay can also be used to determine the health of an organism. Thus, overcrowding in, e.g., an oyster bed may be detected before productivity falls, with this method. The same may be used to assay the health of animals on a particular farm, or on a particular diet. Human ill-health may similarly be detected prior to clinical symptom manifestation. In certain diseases, such as many cancers, this early detection may be critical.

Alternative assays include LISA (liposomal immunosorbent assay) in which a phospholipid which is chemically linked to an antibody is incorporated in a liposome concentrating a fluorescent dye or other indicator. Antibody bound to shock protein produced by the organism being assayed is separated from unbound antibody and detected by the release of the indicator from the opened liposomes.

By using this assay, extremely low levels of environmental pollution, or other distress of the organism can be detected. The relative health of the organism can also be determined or monitored.

As noted, virtually any organisms naturally present in the environment can be evaluated for this assay. Preferred organisms are those that are easily raised in the laboratory, and dominant in the environment. As an example, copepods, for an aquatic environment, such as Chesapeake Bay, are a highly suitable subject. Other aquatic subjects include mysid shrimp, decapod larvae and bivalve larvae. It should be stressed, however, that these organisms are particularly suitable because of the ease with which they may be raised and maintained in the laboratory. Virtually all eukaryotes appear to produce the shock proteins in response to a wide variety of stresses, imposed by the environment, and accordingly, are suitable subjects. If desired, even higher mammals and humans may be used as test species. In the case of higher mammals and humans, where damage to the organism from sampling is not acceptable, blood samples may be taken, tissues sampled from, e.g., the buccal cavity, or similar harmless sampling can be practiced.

It should be further noted that studies indicate that most, if not all organisms in question produce an increasing amount of shock protein in response to an increased amount of stress such as an increased concentration of pollutant. Thus, an assay which gives quantitative information will provide quantitative information as to the degree of pollution or environmental change or stress exerted on the organism.

Further, as noted above, different pollutants give rise to the production of different stress proteins, in various organisms. As an example, stress created by elevated temperature, i.e., heat shock, gives rise to the expression, in Eurytemora of a family of five heat shock proteins, having an approximate molecular weight of 24.5, 70, 82, 98 and 109 KD, respectively. In contrast, the presence of an oxidant, such as chlorine, in a relatively small concentration of 35 ppb gives rise to a family of four shock proteins, having molecular weights of 24, 48, 52 and 70 KD, respectively. A different, common pollutant, tributyltin, at a concentration of 0.5 μg/l gives rise to yet a third family of shock proteins, having molecular weights of 25, 43, 46 and 70 KD, respectively. It is quite clear that a differential assay employing antibodies selected for the varying shock proteins, can indicate, by a combination of positive and negative reactions, what particular type of stress, or stressor, is responsible for the environmental insult. As noted, these antibodies can be prepared through conventional injection of a host, such as a rabbit or a mouse, with the protein, and obtaining from the serum of the host, the antibody responsive thereto. Alternatively, monoclonal antibodies may be prepared and harvested from dedicated cell lines.

EXAMPLES

The invention can be further understood by reference to an ELISA employed to determined the presence of heat shock proteins in copepods.

EXAMPLE I

The basic method was demonstrated using heat shocked copepods tested immunologically for the presence of a major heat shock protein, Hsp 70.

Copepods were collected from the Chesapeake Bay by filtration and washed 3-4 times with sterile bay water. They were incubated overnight in sterile Chesapeake bay water at 15° C.

The copepods were placed at 30° C. to heat shock them for 5 hours. Control animals were kept at 15° C.

After the heat shock period, the copepods were transferred to a small homogenizer and washed twice with phosphate buffered saline (PBS) containing 1.0 mM PMSF (a protease inhibitor). The volume was then reduced to 1 micro l/copepod and the animals homogenized. After homogenization, the sample was centrifuged in a microfuge for 5 minutes to remove particulate matter.

At this point, the protein concentration was determined by the Lowry method. The average usually is 1 μg protein/animal and the samples diluted to a concentration of 5 μg/50 ml with MOPS (a biological buffer).

The samples were assayed for the presence of the major heat shock protein Hsp 70 using a standard ELISA (Enzyme linked immunosorbent assay). After 50 μl of the test solution had been added to the wells of a ELISA plate and incubated for 1 hour, remaining binding sites were blocked with gelatin for a further hour. Primary antibody to Hsp 70 (diluted 1:100) was then added to the wells and again incubated for 1 hour. A secondary (anti-rabbit) antibody was added to detect bound primary antibody. An enzyme (phosphatase in this case) had been conjugated to the secondary antibody, allowing simple detection by the addition of PNP color reagent.

Figure 2:
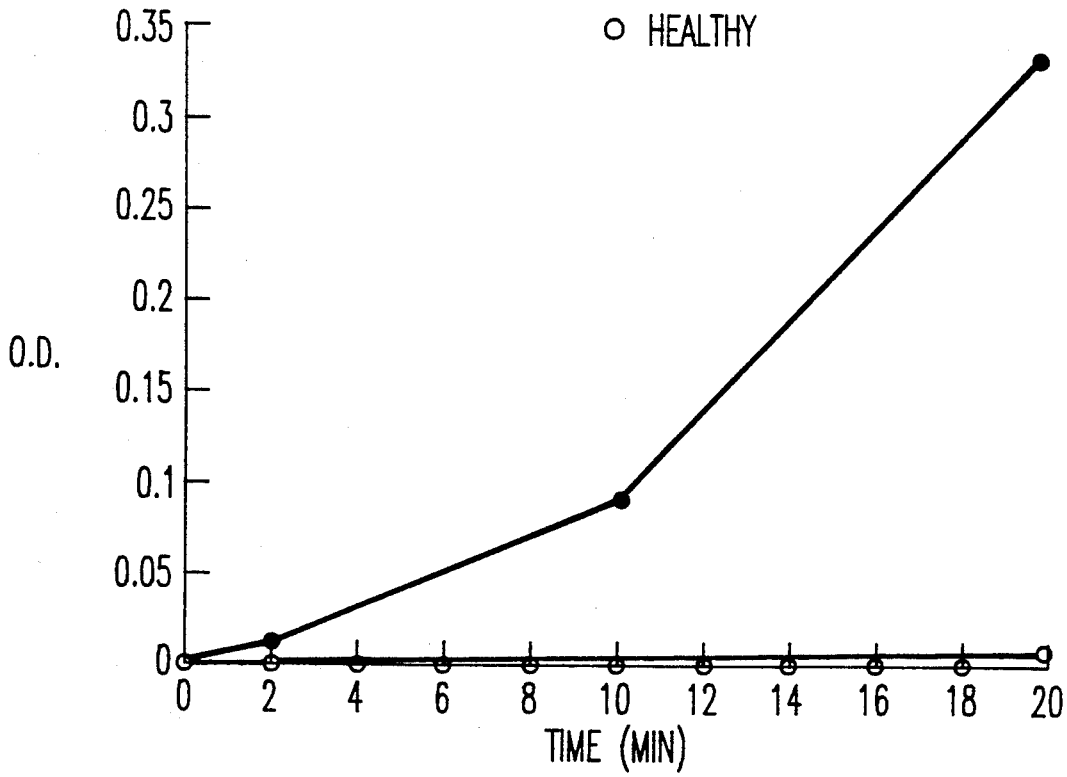

Densities of colors could be observed visually. Wells in columns 1, 3 and 5 were blocked with gelatin, as just described, but wells in columns 7, 9 and 11 were not. Columns 1 and 7 includes samples from copepods heat shocked for five hours, 3 and 9 were tests of samples from control (15° C.). Columns 5 and 11 are wells without sample antigen. The differences between heat shocked and controls (columns 1 and 3 or 1 and 5) could be clearly observed. Graphs have been made of three replicate tests. These are FIGS. 1, 2 and 3.

The primary antibody used in the assay was derived from a 23-amino acid peptide synthesized to maximize homology among human, rat, mouse, and chicken Hsp 70. The antiserum was obtained from rabbits injected with a conjugant of the peptide and BSA (bovine serum albumen). This peptide 70 antibody is extremely reactive in a range of species, including so far, oysters, two species of clams, brine shrimp, striped bass, carrots, sea cucumbers, amphipods, mysid shrimp, caddisfly larvae and, of course copepods. Since the peptide sequence was from mammals, the range of species testable with this antibody will be even wider. The range of stressors (and habitats in land, and in water) is also very wide given the fact that the Hsp 70 responds to almost all stressors.

As previously observed, this is a conventional ELISA system, but is not limiting. Field versions of the assay could include primary antibody coated on polystyrene beads so that the antibody, rather than the antigen would be bound initially. Antigen bound to the antibody in the beads would then be detected, by a second antibody conjugated to an enzyme, to be detected by a color reagent. Neither the enzyme, nor the reagent is critical. The enzyme may even be replaced by a liposome, and the reagent be a fluorescent marker, or a marker detectable under infrared, ultraviolet or x-ray conditions.

EXAMPLE II

To demonstrate the stress protein responsive organisms to chemical stressors, test organisms are exposed to the environment containing the pollutant for a time sufficient to permit stress protein synthesis to be fully induced, while normal protein synthesis is inhibited. Instead of an ELISA assay for convenience, and autoradiographic assay may be used. In this case, after stress protein synthesis is induced, a radioactively labeled amino acid (e.g., 35 S methionine) can be added, to be taken up by the organisms in question. The same labeled amino acid is introduced to the control organisms. Protein synthesis in response to stress can be determined by comparison between the autoradiographs obtained.

Copepods (*Eurytemora affinis*) were exposed to chloride oxidant, for a period of three days, at various levels (0.35, 0.52, 0.70 and 1.40 ppm). The protein signature at each level is remarkably similar, and quite distinct from that produced by the control organisms, or those subjected to heat shock. Specifically, four distinct proteins, having a molecular weight of 24, 48, 52 and 70 KD are reflected in the autoradiogram obtained.

EXAMPLE III

Different chemical pollutants induce the production of different stress protein families. In a fashion similar to Example II above, mysid shrimp were exposed to varying levels of tributyltin, a common chemical pollutant, at a temperature of 21°-23° C., over a nine day chronic survival test. At levels above 0.025 mg/L, including levels of 0.05, 0.1 and 0.2 mg/L, four distinct proteins, having molecular weights of 25, 43, 46 and 70 KD are detected. Interestingly, exposure to a concentration of TBT at 0.025 mg/L did not result in the expression of proteins identified as stress proteins.

It should be further noted, that like heat shock, and a wide variety of other stress conditions, each stressor introduced induced the synthesis of Hsp 70, or a close variant thereof, suggesting the utility of this particular stress protein as an assay target.

Obviously, numerous modifications and variations of the present invention are possible in light of the above teachings. In particular, it is noted that the identity of the host organism(s) involved for sampling, the nature of the environmental stressor(s), and the particular stress protein assayed for, and assay protocol can be varied, given the environment and abilities of the laboratory involved. It is therefore to be understood that within the scope of the appended claims, the invention may be practiced otherwise then as specifically described herein.

What is claimed is:

1. A biological, sublethal assay to determine the presence of specific chemical pollutants in an aquatic environment comprising:
   1) cultivating a population of an organism common to said aquatic environment which produces shock proteins in response to stress induced by chemical pollutants,
   2) exposing a portion of said population to the environment to be assayed, for the period of time sufficient to induce production of stress proteins by said exposed population, if a chemical pollutant stressor is present in the environment,
   3) determining the type of stress proteins produced by said organisms exposed to said environment and
   4) determining the identity of the chemical pollutant by correlating it with the type of stress proteins produced by said population exposed to said environment.

2. The assay of claim 1, wherein said population is cultivated in a controlled condition, and then placed in the environment.

3. The assay of claim 1, wherein said exposed population is assayed for the presence of at least three different stress proteins, the stress proteins being identified and correlated to a specific environmental chemical pollutant.

4. The assay of claim 1, wherein said organism is selected from the group consisting of oysters, clams, brine shrimp, striped bass, carrots, sea cucumbers, amphipods, mysid shrimp, caddisfly larvae, copepods and mixtures thereof.

5. The assay of claim 1, wherein said stress protein assayed for comprises Hsp 70.

6. The assay of claim 1, wherein the amount of chemical pollutant stressor present in the environment is determined by determining the amount of the type of stress protein, and wherein the amount of stress protein present correlates to the amount of chemical pollutant stressor present.

* * * * *